United States Patent

Tanaka et al.

Patent Number: 5,965,407
Date of Patent: Oct. 12, 1999

[54] ANTHRACYCLINE COMPOUND 0624

[75] Inventors: Yasushi Tanaka; Yuzuru Mikami; Katsukiyo Yazawa, all of Chiba-ken, Japan

[73] Assignee: Higeta Shoyu Co. Ltd., Tokyo, Japan

[21] Appl. No.: 09/033,856

[22] Filed: Mar. 3, 1998

[30] Foreign Application Priority Data

Mar. 14, 1997 [JP] Japan ................................. 9-079205

[51] Int. Cl.$^6$ .......................... A61K 31/71; C07H 15/24; C12P 19/56
[52] U.S. Cl. ................. 435/78; 514/34; 536/6.4
[58] Field of Search ............... 536/6.5; 574/35; 438/78

[56] References Cited

U.S. PATENT DOCUMENTS 5,049,549 9/1991 Kolar et al. .......................... 574/34

OTHER PUBLICATIONS

Ruimy, Raymond et al., "*Nocardia pseudobrasiliensis* sp. nov., a new species of Nocardia which groups bacterial strains previously identified as *Nocardia brasiliensis* and associated with invasive diseases.", International Journal Of Systematic Bacteriology, vol. 46, No. 1, pp. 259–264 (1996).

"The Essentials of Antibiotics.", 4th Ed., Japan Chemotherapy Association, Tokyo University Press (1992).

*Primary Examiner*—Elli Peselev
*Attorney, Agent, or Firm*—Browdy and Neimark

[57] ABSTRACT

The present invention relates to compound 0624 having excellent antitumor activity and antimicrobial activity, which is represented by the general formula (1), and a pharmaceutically acceptable salt thereof.

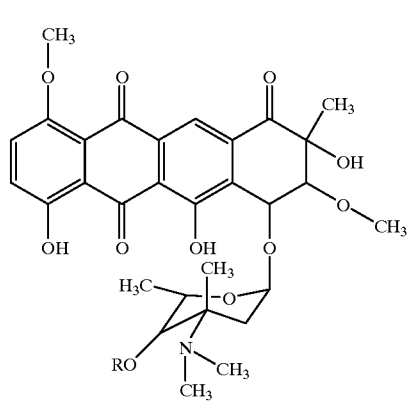

(wherein R represents H or COCH$_3$.)

15 Claims, No Drawings

ANTHRACYCLINE COMPOUND 0624

DETAILED DESCRIPTION OF THE INVENTION

1. Technical Field to which the Invention Belongs

The present invention relates to a novel compound 0624, a method for producing the same and the use thereof. The novel compound 0624 is a novel anthracycline compound heretofore unknown, which is isolated and purified from microbial culture, particularly the culture of actinomycetes, and the compound has excellent physiological activity, particularly excellent antitumor activity and antimicrobial activity.

Thus, the novel anthracycline compound of the present invention can be used effectively as a prophylactic agent and/or therapeutic agent of diseases, namely as antitumor agent and antimicrobial agent.

2. Prior Art

A large number of novel compounds have been discovered or synthesized as antitumor agents, and some of these compounds have practical use.

Various antitumor agents heretofore known are surely excellent, but further improvement thereof has been demanded in the respect of safety and productivity in addition to efficacy. The same is true with antimicrobial agents.

Problems to be Solved by the Invention:

The present invention has been achieved to satisfy these demands in the industry. After extensive screenings following the technical development of antitumor agents, the inventors have found that a novel compound heretofore unknown has an antitumor activity and antimicrobial activity. Thus, the present invention has been achieved. It is an object of the present invention to provide a novel compound with far more excellent antitumor activity and antimicrobial activity than those of substances heretofore known.

Means for Solving the Problems:

In order to obtain a substance with novel antitumor activity and antimicrobial activity, the present inventors have made extensive screenings in products of natural origin, particularly metabolic products of microorganisms so as to find a substance with more effective antitumor activity and antimicrobial activity. The inventors have found that a substance with the objective properties is accumulated in the cells and culture broth of *Nocardia pseudobrasiliensis* ATCC 51512 and 202184. Furthermore, the inventors have examined the physicochemical properties of the substance in detail, and revealed its chemical structure. Then, it is confirmed that the substance is a novel substance heretofore unknown. As described in claim 1, the substance is a novel anthracycline compound represented by the general formula (1). The present inventors have designated the compound as 0624.

More specifically, the present invention relates to a novel compound 0624 represented by the following general formula (1) or a pharmaceutically acceptable salt thereof.

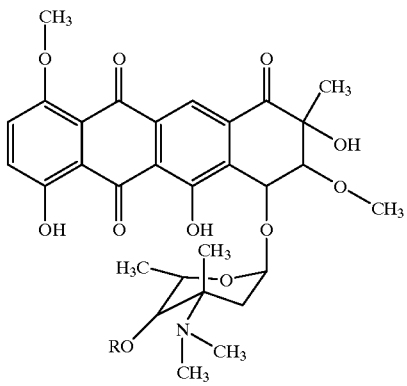

(1)

(wherein R represents H or $COCH_3$.)

Furthermore, the present invention also relates to a novel antitumor agent and a novel antimicrobial agent, containing the novel anthracycline compound 0624 or a pharmaceutically acceptable salt thereof, as the effective ingredient.

The present invention will now be described in detail hereinbelow.

Embodiments for Carrying out the Invention:

Compound 0624 in accordance with the present invention is a mixture, and currently, two compounds, namely compound A of the general formula (1) wherein R is H and compound B of the general formula (1) wherein R is $COCH_3$, are isolated.

The physicochemical properties of these compounds A and B are individually shown in the following Tables 1 and 2.

TABLE 1

Physicochemical properties of compound 0624-A

1. Color and state of the substance: reddish microcrystals
2. Infrared absorption spectrum
   Significant signals are as follows;
   ($\lambda$max) cm$^{-1}$: 719, 796, 831, 957, 991, 1022, 1131, 1203, 1205, 1378, 1407, 1434, 1462, 1536, 1616, 1677, 2990, 3425
3. Ultraviolet absorption spectrum:
   Significant signals are as follows;
   ($\lambda$max) nm: 490 (broad absorption)
4. Molecular weight: 585
5. Molecular formula: $C_{30}H_{36}NO_{11}$
6. FAB - MS:
   Found: 586.23028 (M + H)$^+$
   Calculated: 586.23013 ($C_{30}H_{36}NO_{11}$)
7. $^1$H NMR spectrum:
   Significant signals are as shown in Table 3.
8. $^{13}$C NMR spectrum:
   Significant signals are as shown in Table 3.
9. Solubility:
   Soluble in water, methanol, ethanol, DMSO and ethyl acetate.
   Insoluble in chloroform, ether and hexane.

TABLE 2

Physicochemical properties of compound 0624-B

1. Color and state of the substance: reddish microcrystals
2. Infrared absorption spectrum:
   Significant signals are as follows;
   ($\lambda$max) cm$^{-1}$: 716, 760, 795, 831, 988, 1024, 1033, 1101, 1131, 1180, 1206, 1285, 1375, 1402, 1436, 1466, 1619, 1669,

TABLE 2-continued

Physicochemical properties of compound 0624-B 1742, 2930, 3405
3. Ultraviolet absorption spectrum:
   Significant signals are as follows;
   (λmax) nm: 490 (broad absorption)
4. Molecular weight: 627
5. Molecular formula: $C_{32}H_{38}NO_{12}$
6. FAB - MS:
   Found: 628.2417 $(M + H)^+$
   Calculated: 628.2394 $(C_{32}H_{38}NO_{12})$
7. $^1H$ NMR spectrum:
   Significant signals are as shown in Table 4.
8. $^{13}C$ NMR spectrum:
   Significant signals are as shown in Table 4.
9. Solubility:
   Soluble in water, methanol, ethanol, DMSO and ethyl acetate.
   Insoluble in chloroform, ether and hexane.

On the $^1H$ NMR and $^{13}C$ NMR spectra of these compounds A and B, significant signals are shown in the following Tables 3 and 4.

TABLE 3

$^1H$- and $^{13}C$-NMR data of compound 0624-A (CD$_3$OD) (a: δ in ppm)

| Position | $^1H$ | $^{13}C$ |
|---|---|---|
| 1 | | 156.6 |
| 2 | 7.65 (d, 9.5) | 126.6 |
| 3 | 7.47 (d, 9.5) | 128.7 |
| 4 | 12.08 (s) | 158.8 |
| 4a | | 116.5 |
| 5 | | 193.5 |
| 5a | | 119.5 |
| 6 | 12.51 (s) | 162.9 |
| 6a | | 133.1 |
| 7 | 5.15 (d, 2.2) | 74.0 |
| 8 | 3.72 (d, 2.2) | 87.9 |
| 9 | | 77.6 |
| 10 | | 199.8 |
| 10a | | 137.4 |
| 11 | 8.10 (s) | 117.0 |
| 11a | | 136.3 |
| 12 | | 180.8 |
| 12a | | 119.1 |
| 13 | 3.99 (s) | 57.3 |
| 14 | 1.50 (s) | 24.0 |
| 15 | 3.56 (s) | 60.2 |
| 1' | 5.76 (d, 4.1) | 102.2 |
| 2' | 2.11 (d, 13.4, 4.1) | 34.0 |
|    | 2.28 (d, 13.4) | |
| 3' | | 66.1 |
| 4' | 3.66 (s) | 69.5 |
| 5' | 4.23 (q, 6.6) | 66.3 |
| 6' | 1.41 (d, 6.6) | 17.4 |
| 7' | 1.45 (s) | 14.9 |
| 8' | 2.71 (s) | 37.2 |
| 9' | 2.76 (s) | 36.3 |

TABLE 4

$^1H$- and $^{13}C$-NMR data of compound 0624-B (CD$_3$OD) (a: δ in ppm)

| Position | $^1H$ | $^{13}C$ |
|---|---|---|
| 1 | | 154.5 |
| 2 | 7.74 (d, 9.6) | 125.8 |
| 3 | 7.47 (d, 9.6) | 126.9 |
| 4 | 12.07 (s) | 156.4 |
| 4a | | 115.6 |
| 5 | | 191.8 |

TABLE 4-continued $^1H$- and $^{13}C$-NMR data of compound 0624-B (CD$_3$OD) (a: δ in ppm)

| Position | $^1H$ | $^{13}C$ |
|---|---|---|
| 5a | | 134.9 |
| 6 | 12.52 (s) | 160.8 |
| 6a | | 131.0 |
| 7 | 5.03 (d, 2.2) | 72.0 |
| 8 | 3.54 (d, 2.2) | 86.3 |
| 9 | | 75.9 |
| 10 | | 198.7 |
| 10a | | 135.7 |
| 11 | 8.01 (s) | 114.9 |
| 11a | | 118.4 |
| 12 | | 178.9 |
| 12a | | 118.1 |
| 13 | 3.93 (s) | 56.8 |
| 14 | 1.39 (s) | 23.5 |
| 15 | 3.43 (s) | 59.6 |
| 1' | 5.76 (d, 4.2) | 99.6 |
| 2' | 2.02 (d, 13.5, 4.2) | 32.9 |
|    | 2.15 (d, 13.5) | |
| 3' | | 62.7 |
| 4' | 5.14 (s) | 69.4 |
| 5' | 4.27 (q, 6.5) | 64.2 |
| 6' | 1.14 (d, 6.5) | 17.1 |
| 7' | 1.43 (s) | 14.5 |
| 8' | 2.68 (d, 4.4) | 37.1 |
| 9' | 2.55 (d, 4.5) | 36.0 |
| 1" | | 170.6 |
| 2" | 2.29 (s) | 20.8 |

Compound 0624 of the present invention is produced by, for example, *Nocardia pseudobrasiliensis* ATCC 51512 and 202184.

*Nocardia pseudobrasiliensis* ATCC 51512 and 202184 is a type strain of species *Nocardia pseudobrasiliensis* and has been deposited under the aforementioned accession No. in ATCC (American Type Culture Collection). The bacterial strain was isolated from the leg tumor of a patient with ulcerative colitis, which is a bacterial strain classified as a novel species not belonging to any species of genus Nocardia, by Ruimy (Int. J. Syst. Bacteriol., 46, 259–264 (1996)).

It has been confirmed that compound 0624 of the present invention is produced not only by *Nocardia pseudobrasiliensis* ATCC 51512 and 202184 but also by other bacterial strains of genus Nocardia. The production of compound 0624 encompasses the use of any mutant strains capable of producing compound 0624, including artificial mutant strains of these microorganisms, generated by mutation process by means of X-ray irradiation, γ-ray irradiation, nitrogen mustard, N-methyl-N'-nitro-N-nitrosoguanidine, 2-aminopurine, ethylmethane sulfonate or the like as well as spontaneous mutant strains of these microorganisms.

The novel compound 0624 represented by the general formula (1) in accordance with the present invention can be produced not only by chemical synthesis but also by the microorganisms as described above.

In the latter case, the novel compound 0624 represented by the general formula (1) can be produced by culturing a bacterium capable of generating the compound and belonging to the genus Nocardia, in a culture medium containing a carbon source and a nitrogen source which can be assimilated by, for example, *Nocardia pseudobrasiliensis* ATCC 51512 and 202184, preferably under aerobic submerged culture conditions (for example, agitation culture, aerated agitation culture and the like).

As the carbon source to be used, preferably, glucose, glycerol, sucrose, starch, dextrin, and other carbohydrates are desirable.

As the nitrogen source to be used, oatmeal, yeast extract, beef extract, tuna meat extract, peptone, gluten meal, cottonseed powder, soybean meal, corn steep liquor, dry yeast, wheat germ, peanut powder, chicken bone meat meal and the like are desirable. As the nitrogen source, inorganic and organic nitrogen compounds, such as ammonium salt (for example, ammonium nitrate, ammonium sulfate, and ammonium phosphate), urea, and amino acid, can also be used advantageously.

These carbon sources and nitrogen sources are advantageously used in combination, and they are not necessarily pure. When they are not pure, they contain growth factors and trace elements, which are preferably used.

If necessary, inorganic salts, such as sodium carbonate, potassium carbonate, sodium phosphate, potassium phosphate, sodium chloride, potassium chloride, sodium iodide, potassium iodide, magnesium salts, copper salts, and cobalt salts, can be added to the culture medium.

If necessary, particularly if the culture medium is foaming, antifoaming agents, such as fluid paraffin, animal oils, vegetable oils, mineral oils and silicone, can be added to the medium.

For industrially producing the objective substance on a large scale, aerated agitation culture is preferable as in the case of other fermentation products. For the production on a small scale, shaking culture by means of a flask is preferable.

For culturing in a large tank, furthermore, a preferable process for producing of compound 0624 comprises firstly inoculating and culturing the producing bacteria in a relatively small amount of the culture medium and then transferring the resulting culture medium to a large production tank for productive culturing, so as to prevent the delay of the growth of the bacteria in the production process of compound 0624.

In this case, the composition of the culture medium to be used for preliminary culturing and the composition thereof to be used for productive culturing may be the same or different if necessary.

Culturing is preferably carried out under aerated agitation conditions, by appropriately employing known means, such as agitation with a propeller or other machine, rotation or shaking of fermentor, pump process, and air aeration. The air for aeration is preferably sterilized.

The culturing temperature may appropriately vary within a range where the bacteria producing compound 0624 can produce the compound, but generally, the bacteria are preferably cultured in a temperature range of 10 to 40° C., preferably 25 to 35° C.

The culturing time varies depending on the culturing conditions and culturing volume, but generally, the time is about one day to about one week.

After termination of the culturing, the objective compound 0624 is recovered from the culture. More specifically, from the cells, compound 0624 can be recovered and purified by routine methods, via direct extraction with water and/or organic solvent or, via mechanical disruption or disruption by known means such as ultrasonication and subsequent extraction with water and/or organic solvent. From the culture broth, compound 0624 may be directly extracted with solvent; or compound 0624 may be recovered by filtration or centrifugation of the culture broth, concentration under reduced pressure, lyophilizing, pH adjustment, absorption of compound 0624 by contact with carrier such as anion or cation exchange resin, active charcoal, powdery cellulose, silica gel, alumina and absorption resins, and then elution of the compound from the carrier.

As the recovery and purification method, routine methods for antibiotics recovery can be used appropriately; for example, routine processes such as solvent extraction with water, organic solvent or mixtures of solvents thereof, chromatography, recrystallization from a single solvent or a mixture of solvents, may appropriately be used, singly or in combination.

The recovery and purification of compound 0624 are carried out by appropriately utilizing known processes as described above, but for example, the following process may also be satisfactory.

By treating the culture through centrifugation or through MF membrane, the cells are fractionated from the culture supernatant, and both the fractions are extracted with ethyl acetate, followed by concentration under reduced pressure, and silica gel chromatography for the absorption of the compound, which is then subjected to step-wise elution processes in chloroform—methanol and acetone—methanol, for further fractionation. Then, the objective fraction is purified by high-performance liquid chromatography, and then lyophilized, if necessary.

When compound 0624 of the present invention is administered as a pharmaceutical agent, the compound can be administered as it is or the compound can be administered as a pharmaceutical composition containing the compound at 0.1% to 99.5%, preferably 0.5% to 90% in a pharmaceutically acceptable carrier, nontoxic and inactive.

As the carrier, use is made of diluent in solid, semi-solid, or liquid, filler and one or more of other formulation auxiliary agents. The pharmaceutical composition is preferably administered in a dosage unit form. The pharmaceutical composition of the present invention may be administered orally, inside tissues, locally (trans-dermal administration and the like), or trans-rectally, and the composition may be used even as an external preparation. The composition should essentially be administered in a dosage form suitable for such administration.

The dose of the compound as an antitumor agent or an antimicrobial agent preferably varies, depending on the conditions of a patient, such as age and body weight, administration route, the performance and seriousness of the disease, but generally, the compound is administered within a range of 10 to 2000 mg/day on the basis of the effective ingredient of the present invention per adult. In some case, the dose may satisfactorily be less or the dose may necessarily be higher than the level. If the compound should be administered at a high dose, the compound should preferably be divided in several doses per one day.

The oral administration can be carried out in a solid or liquid dose unit, for example, powder, mixed powder, tablet, sugar coated tablet, capsule, drop, sublingual tablet and other dosage forms.

Powder can be produced by preparing the active substance into suitable fineness. Mixed powder can be produced by preparing the active substance into suitable fineness and mixing then the resulting substance with pharmaceutical carrier preliminarily prepared similarly into fineness, for example, edible carbohydrate such as starch and mannitol. If necessary, flavor, preservative, dispersing agent, coloring agent, fragrance and the like may be mixed with them.

A capsule can be produced, by filling preliminarily prepared powder, mixed powder or granules inside a capsule outer shell such as a gelatin capsule. Lubricant and fluidizing agent, for example, colloidal silica, talc, magnesium stearate, calcium stearate, solid polyethylene glycol, may be mixed therewith, and the resulting mixture is subsequently subjected to filling process. If disintegrator or solubilizing agent, for example carboxymethyl cellulose, calcium carbonate and sodium carbonate, is added, the efficacy of the pharmaceutical agent in the resulting capsule after administration can be improved.

Compound 0624 in microfine powder may be suspended and dispersed in vegetable oil, polyethylene glycol, glycerin, and surfactant, and the resulting suspension may be wrapped with a gelatin sheet to prepare a soft capsule.

A tablet can be produced by preparing a powdery mixture containing compound 0624, granulating or slugging the mixture, subsequently adding disintegrator or lubricant to the resulting granules or slugs prior to tableting.

As to the powdery mixture, an appropriately prepared compound 0624 may be mixed with the aforementioned diluent or bases, in combination with binder (for example, sodium carboxymethyl cellulose, alginate salt, gelatin, polyvinyl pyrrolidone, and polyvinyl alcohol), dissolution delaying agent (for example, paraffin), re-absorption agents (for example, quaternary salt) and/or absorption agents (for example, bentonite, kaolin, and dicalcium phosphate), if necessary. The powdery mixture can be prepared into granules, by moistening the mixture with binder such as syrup, starch paste, gum arabic, cellulose solution or polymer solution, and subsequently passing the moistened mixture through a screen in an enforcing manner. Instead of such granulation of the powdery mixture, the powdery mixture may be applied to a tableting machine and the obtained slugs of an incomplete shape are disrupted to give granules.

By adding stearic acid, stearate salts, talc, mineral oil or other as lubricant to the granules, the sticking of the granules can be prevented. Then, the mixture thus lubricated is tableted. Without carrying out the granulation or slugging described above, compound 0624 may be mixed with a fluid inactive carrier and tableted directly. Transparent or semitransparent protective film, comprising shellac sealing coating, coating with sugar or a polymer material, or polished coating comprising wax, may also be used.

Other oral dosage forms, for example, solution, syrup, and elixir, may be prepared as a dose unit form so that may contain compound 0624 of a given amount. Syrup is produced by dissolving the compound in an appropriate aqueous flavored solution; and elixir is produced by dispersing the compound in a non-toxic alcohol carrier. Solubilizer, emulsifier (for example, ethoxylated isostearyl alcohol, and polyoxyethylene sorbitol ester), preservative, flavoring agent (for example, peppermint oil, and saccharin) and others, may be added, if necessary.

If necessary, the dosage unit formulation for oral administration may be micro-encapsulated. The formulation may be coated or embedded in polymer or wax, to procure prolonged action time or sustained release.

Parenteral administration can be done by using liquid dosage unit form, for example in solution or suspension, such as subcutaneous injection, intra-muscular injection and intravenous injection. These can be produced by suspending or solubilizing a given amount of compound 0624 in a non-toxic liquid carrier suitable for injection purpose, for example, aqueous or oily media, and subsequently sterilizing the suspension or solution. Otherwise, a given amount of the compound is placed in a vial, and thereafter, the vial and the contents therein may satisfactorily be sterilized, prior to sealing of the vial. For dissolution or mixing immediately prior to administration, a preliminary vial or carrier may be prepared, along with the compound in powder or lyophilized powder. For preparing an isotonic injection, non-toxic salt or salt solution may be added. Furthermore, stabilizer, preservative, emulsifier and the like, may be used in combination.

Rectal administration can be carried out by using a suppository produced by mixing compound 0624 with a solid having a low melting point, such as polyethylene glycol, cacao oil, higher ester (for example, palmitate myristylester) and mixture thereof.

Compound 0624 (sometimes simply referred to as "0624" hereinbelow) has excellent physiological activity and also antitumor activity and antimicrobial activity, as apparently understood in the following examples.

The present invention will now be described in detail in the examples, but the invention is not limited to the examples.

EXAMPLES

Example 1

1. Fermentation Production

*Nocardia pseudobrasiliensis* ATCC 51512 and 202184 was inoculated in an essential medium (5 ml) comprising 2% glycerol, 1% polypeptone (manufactured by Nippon Seiyaku, Co.), and 0.5% tuna meat extract, pH 7.0, as divided in a 10 ml-Erlenmeyer flask, and subject to shaking culture at 30° C. for 72 hours.

Furthermore, the thus-obtained seed culture was then inoculated at 1% v/v in the same medium (200 ml) divided in a 500-ml flask and subjected to preliminary culturing under the same conditions. The thus-obtained preliminary culture was inoculated in the same medium (15 liters) in a 20-liter culture tank, which was therein cultured at agitation of 250 rpm and aeration of 15 liters per minute, at 30° C. for 120 hours.

2. Recovery and Purification

The resulting culture (15 liters) was filtered through a filter cloth, to separate the cells and the culture supernatant (broth), which were then recovered. To the cells was added methanol (2 liters) for extraction procedure. The extracted solution was further extracted in ethyl acetate (2 liters). Alternatively, the culture supernatant was concentrated under reduced pressure, which was then adjusted to pH 9.0, prior to extraction into ethyl acetate (2 liters). Both the extracted fractions were mixed together, and the resulting mixture was subjected to the following purification process.

The fraction extracted into ethyl acetate (i.e., said mixture) was concentrated with an evaporator and dried, and the dried residue was dissolved in chloroform (30 ml), and subjected to silica gel chromatography (column; 3 cm×30 cm). The elution solvents used were chloroform:methanol (10:0; 1 liter) and chloroform:methanol (10:1; 1 liter) and chloroform:methanol (3:1; 1 liter), for step-wise elution. Because compound 0624 has an antimicrobial activity, the compound in the eluted fractions was detected by paper disk method (The Essentials of Antibiotics, the 4-th edition, Tokyo University Press, 1992), using as the indicator the growth inhibitory activity against a test microorganism *Micrococcus luteus*. The active fraction eluted with chloroform:methanol (3:1) was further fractionated and purified by high-performance chromatography (HPLC) on an ODS column (SOKEN pack: 20×250 mm). Elution was done by using acetonitrile:aqueous 0.2% trifluoroacetic acid solution (22:78) at a flow rate of 10 ml/min. The active fractions were collected by using as the indicator the absorbance at 229 nm and the growth inhibitory activity against *Micrococcus luteus*. Two fractions individually at retention times of 35 minutes and 91 minutes were collected. Compound 0624-A as the 35 min-fraction was 23 mg in dry weight; compound 0624-B as the 91 min-fraction was 11 mg in dry weight.

Example 2

Antitumor Activity

Cell suspensions were prepared (at $5.6 \times 10^6$ cells/ml) by using RPMI 1640 medium for L1210 cell line, RPMI 1640 medium containing 20 $\mu$M 2-mercaptoethanol (all the media containing 10% bovine serum) for P388 cell line and an adriamycin resistant P388 cell line, Eagle's MEM medium for KB cell line, and $\alpha$-MEM medium for CHO cell line.

Test samples (0624-A and 0624-B) were individually dissolved in methanol and serially diluted with the individual media in a series of 2-fold dilution starting from a concentration of 0.1 mg/ml. The cell suspensions (each of 180 $\mu$l) and each test sample (20 $\mu$l) were divided in a 96-well microtiter plate, and subjected to culturing in wet atmosphere of 5% $CO_2$ –95% air at 37° C. 72 hours after, cell growth was determined by the calorimetric assay using 3-(4, 5-dimethyl-z-thiazolyl)-2,5-diphenyl-2H-tetrazolium bromide (MTT). More specifically, 20 $\mu$l each of 2 mg/ml MTT solution was added into each well, followed by culturing at 37° C. for 4 hours. Then, 50 $\mu$l of 50 % dimethylformamide solution containing 20% sodium dodecyl sulfate was added to each well, which was left to stand. The resulting formed violet formazan crystal was solubilized and subjected to determination of absorbance at 570 nm, by using a microplate reader (Immunoreader), which was used as the indicator of growth. The results are shown as the concentration of a test sample ($IC_{50}$ value), at which the 50% of the growth was inhibited.

Compounds 0624-A and 0624-B individually have the growth inhibitory activities against the cell lines L1210, P388, adriamycin resistant P388, KB and CHO, and it is confirmed that the compounds are effective as antitumor agents (Table 5).

TABLE 5

Growth inhibitory activities of compounds 0624-A and 0624-B against tumor cells

| | $IC_{50}$ ($\mu$g/ml) | |
|---|---|---|
| Cell lines | 0624-A | 0624-B |
| L1210 | 0.15 | 0.18 |
| P388 | 0.47 | 0.59 |
| Adriamycin resistant P388 | 0.97 | 1.05 |
| KB | 1.06 | 1.32 |
| CHO | 12.3 | 18.6 |

Example 3
Antimicrobial Activity

The antimicrobial activity of compound 0624 was confirmed through the assaying of the minimum growth inhibitory concentration (MIC).

The MICs of compound 0624 against various bacteria were determined in a Muller-Hinton broth (BBL) containing 0.2% glucose, according to the standard defined by the Japan Chemotherapy Association (The Essentials of Antibiotics, the 4-th edition, Tokyo University Press, 1992).

The test bacteria were adjusted to $1 \times 10^8$ cfu/ml in the broth, and then used as test bacteria solutions.

The test samples (compounds 0624-A and 0624-B) were, separately, dissolved in methanol and were then serially diluted with the broth in a series of 2-fold dilution, starting from a concentration of 0.1 mg/ml. Each test bacteria solution (180 $\mu$l) and each test sample (20 $\mu$l) were divided in a 96-well microtiter plate, and cultured at 37° C. After 24 hours, the MIC was observed and calculated by the eye, and the resulting MIC was defined as MIC value.

Both compounds 0624-A and 0624-B exhibited a wide spectrum of antimicrobial activity against gram-positive bacteria (Table 6).

TABLE 6

Antimicrobial activities of compounds 0624-A and D624-B

| | MIC ($\mu$g/ml) | |
|---|---|---|
| Test organisms | 0624-A | 0624-B |
| Micrococcus luteus IFM2066 | 1.56 | 12.5 |
| Staphylococcus aureus 209P | 3.13 | 100 |
| Bacillus subtilis PC1189 | 6.25 | 3.13 |
| Nocardia transvalensis IFM0333 | 3.13 | 6.25 |
| N. brasiliensis IFM0236 | 6.25 | >100 |
| N. otitidiscaviarum IFM0239 | 1.56 | >100 |
| N. nova IFM0290 | 0.78 | 1.56 |
| N. asteroides IFM0319 | 1.56 | 3.13 |
| N. farcinica IFM0284 | 3.13 | 12.5 |
| Mycobacterium smegmatis ATCC607 | 1.56 | 3.13 |
| M. phlei ATCC11758 | 0.78 | 3.13 |
| M. flavescens ATCC14474 | 3.13 | 12.5 |

Advantages of the Invention:

The present invention is to provide compound 0624, being a novel substance and having excellent physiological activity, and therefore, the compound can be used in various pharmaceutical products such as an antitumor agent and an antimirobial agent.

What is claimed is:

1. Compound 0624 of the formula (1) represented by the following chemical formula (1), or a pharmaceutically acceptable salt thereof;

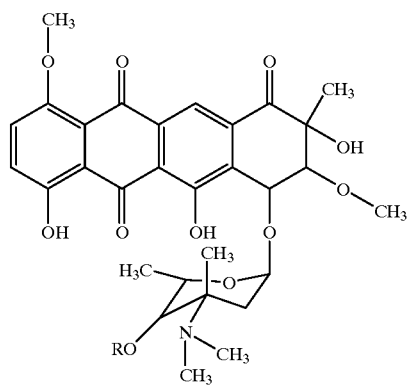

(1)

(wherein R is —H or —COCH$_3$).

2. Compound 0624 according to claim 1, wherein R is —H.

3. Compound 0624 according to claim 1, wherein R is —COCH$_3$.

4. An antitumor agent comprising at least one compound according to claim 1, or a pharmaceutically acceptable salt thereof, as the effective ingredient and a pharmaceutically acceptable carrier or excipient.

5. An antimicrobial agent comprising at least one compound according to claim 1, or a pharmaceutically acceptable salt thereof, as the effective ingredient and a pharmaceutically acceptable carrier or excipient.

6. A method for producing the compound according to claim 1 or a salt thereof, comprising culturing a bacterium belonging to genus Nocardia pseudobrasiliensis and capable of producing the compound according to claim 1, and collecting the compound from the culture.

7. An antitumor agent comprising the compound according to claim 2 or a pharmaceutically acceptable salt thereof, as the effective ingredient, and a pharmaceutically acceptable carrier or excipient.

8. An antimicrobial agent comprising the compound according to claim 2 or a pharmaceutically acceptable salt thereof, as the effective ingredient, and a pharmaceutically acceptable carrier or excipient.

9. A method for producing the compound according to claim 2 or a salt thereof, which comprises culturing *Nocardia pseudobrasiliensis* capable of producing the compound according to claim 2, and collecting the compound from the culture.

10. An antitumor agent comprising the compound according to claim 3 or a pharmaceutically acceptable salt thereof, as the effective ingredient, and a pharmaceutically acceptable carrier or excipient.

11. An antimicrobial agent comprising the compound according to claim 3 or a pharmaceutically acceptable salt thereof, as the effective ingredient, and a pharmaceutically acceptable carrier or excipient.

12. A method for producing the compound according to claim 3 or a salt thereof, which comprises culturing *Nocardia pseudobrasiliensis* capable of producing the compound according to claim 2, and collecting the compound from the culture.

13. The method according to claim 6 wherein the *Nocardia pseudobrasiliensis* is *Nocardia pseudobrasiliensis* ATCC 202184 or a mutant thereof.

14. The method according to claim 9 wherein the *Nocardia pseudobrasiliensis* is *Nocardia pseudobrasiliensis* ATCC 202184 or a mutant thereof.

15. The method according to claim 12 wherein the *Nocardia pseudobrasiliensis* is *Nocardia pseudobrasiliensis* ATCC 202184 or a mutant thereof.

\* \* \* \* \*